United States Patent
Hamill et al.

(10) Patent No.: US 10,682,115 B1
(45) Date of Patent: Jun. 16, 2020

(54) LIGHT WEIGHT POSITRON EMISSION TOMOGRAPHY PHANTOM

(71) Applicant: Siemens Medical Solutions USA, Inc., Malvern, PA (US)

(72) Inventors: James J. Hamill, Knoxville, TN (US); Stefan B. Siegel, Knoxville, TN (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 0 days.

(21) Appl. No.: 16/401,479

(22) Filed: May 2, 2019

(51) Int. Cl.
- A61B 6/00 (2006.01)
- G21F 1/00 (2006.01)
- A61B 6/10 (2006.01)
- G01T 1/29 (2006.01)
- A61B 6/03 (2006.01)
- G01T 7/00 (2006.01)

(52) U.S. Cl.
CPC .............. *A61B 6/583* (2013.01); *A61B 6/037* (2013.01); *A61B 6/107* (2013.01); *G01T 1/2985* (2013.01); *G01T 7/00* (2013.01); *G21F 1/00* (2013.01)

(58) Field of Classification Search
CPC ......... A61B 6/583; A61B 6/037; A61B 6/107; G01T 1/2985; G01T 7/00; G21F 1/00
See application file for complete search history.

(56) References Cited

U.S. PATENT DOCUMENTS

| | | | |
|---|---|---|---|
| 5,502,303 | A | 3/1996 | Gonzalez-Lepera |
| 7,247,844 | B2 * | 7/2007 | Thompson ............ G01T 1/2985 250/252.1 |
| 7,675,028 | B2 | 3/2010 | Breuer et al. |
| 7,965,080 | B2 | 7/2011 | Breuer et al. |
| 8,089,043 | B2 | 1/2012 | Casey et al. |
| 9,459,333 | B2 * | 10/2016 | Bao ...................... G01R 33/481 |
| 9,557,395 | B2 | 1/2017 | Bao et al. |
| 10,162,029 | B2 | 12/2018 | Watson |
| 2009/0283668 | A1 * | 11/2009 | Gilbertson ............. G01D 18/00 250/252.1 |
| 2009/0314933 | A1 * | 12/2009 | Breuer ................... A61B 6/583 250/252.1 |
| 2011/0229055 | A1 * | 9/2011 | Clarke ................... A61B 6/583 382/287 |
| 2015/0212219 | A1 * | 7/2015 | Cerello .................. A61B 6/583 702/104 |

* cited by examiner

*Primary Examiner* — David E Smith

(57) ABSTRACT

A novel PET calibration phantom structure is disclosed that has reduced overall weight and reduced radiation shielding requirement while still enabling safe handling. Furthermore, when the phantom is not being used, the β+ radiation source can be turned off or removed from the phantom, thus, lowering the radiation exposure risk to those handling the phantom.

22 Claims, 3 Drawing Sheets

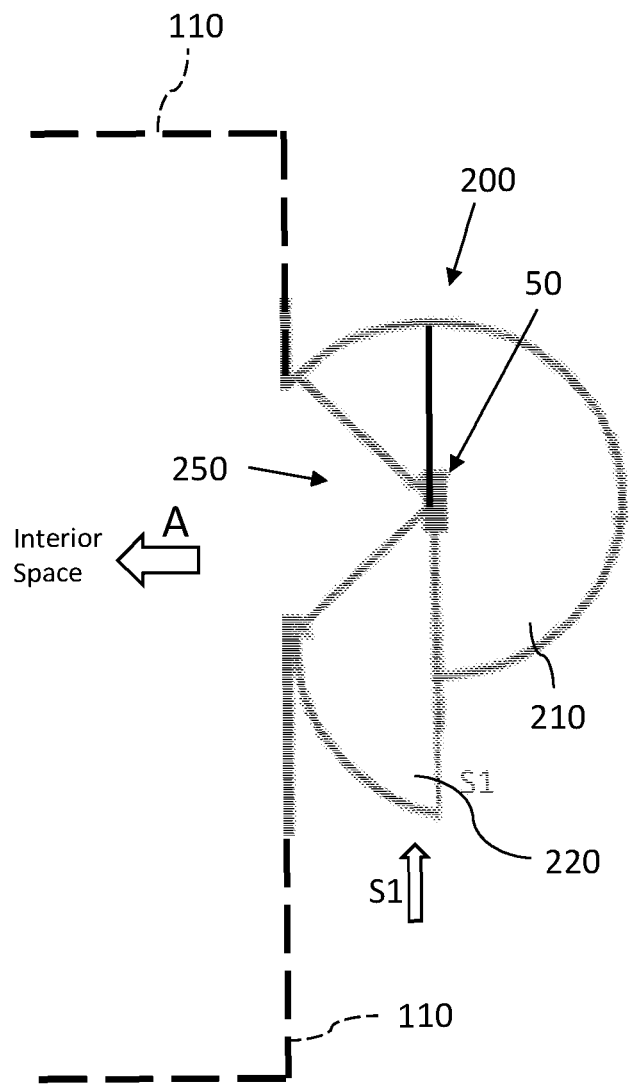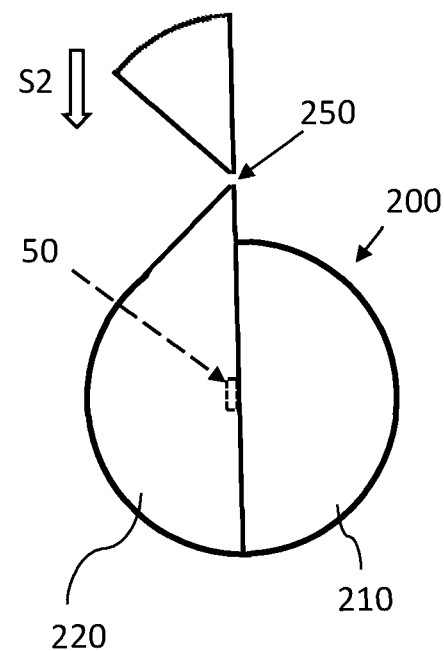
FIG. 2A
FIG. 2B

LIGHT WEIGHT POSITRON EMISSION TOMOGRAPHY PHANTOM

CROSS-REFERENCE TO RELATED APPLICATIONS

None.

FIELD

The present disclosure relates to nuclear medicine. More particularly, this disclosure relates to phantoms used for quality control measurements and calibration of nuclear medical imaging devices.

BACKGROUND

Positron emission tomography (PET) is a nuclear medicine imaging technique that produces a three-dimensional image representing the distribution of positron emitting isotopes within a body. As the radioisotope undergoes positron emission decay (also known as positive beta decay), it emits the antimatter counterpart of electrons. As the positrons lose energy, they ultimately encounter and annihilate with electrons, usually producing a pair of annihilation (gamma) photons moving in opposite directions. The PET system determines the line along which the annihilation occurred, by detecting the pair of gamma photons in time coincidence.

In general, a test object (phantom) is used to calibrate and/or verify (QC) the accuracy of nuclear medical imaging devices such as PET scanners. In essence, a phantom is an object that contains positron (β+) emitting activity in a known shape and distribution throughout its body. Thus, by imaging the phantom, the accuracy of the PET instrument and its software may be assessed and, if necessary, the settings may be adjusted.

Conventionally, PET, PET/CT, and PET/MR systems are quality controlled and calibrated using a cylindrical positron source, also referred to as a phantom, comprised of $^{68}$Ge, as the positron source, dispersed in a solid urethane matrix, and encased in a polyethylene shell. $^{68}$Ge decays to the positron-emitting isotope $^{68}$Ga. The cylindrical shape facilitates subsequent analysis through symmetry. The cylinder is longer than the axial extent of the imaging volume, so dimensions of 21 cm diameter×35 cm long are typical, and they are also quite heavy. As these phantoms are radioactive, they unavoidably expose the operators to some ionizing radiation when positioned within, and removed from, the imaging system. Scaling such phantoms to support systems with ever increasing axial extent is impractical as there is excessive attenuation and scatter of the gamma photons, and the phantoms become excessively heavy and difficult to shield when in storage.

The afore mentioned phantoms are heavy, about 10-15 kg, and require over 100 kg of lead for shielding the technologist, the scanner, patients and other people, from the bulk of the annihilation gamma photons when not in use. These weights impact cost of shipment and facility of handling. Further, the shielding contains lead and as such is a challenge from a hazardous material control perspective.

Thus a need exists for a phantom that can accommodate a PET scanner, a PET/CT scanner, and/or a MR/PET scanner, and overcomes the problems described in the prior art.

SUMMARY

Disclosed herein is a novel PET calibration phantom structure that has reduced the overall weight and radiation shielding requirements, and is safe to handle. This is achieved by confining the β+ emitting radiation source to a small volume, which may be shut off or removed when the phantom is not in use.

A PET calibration phantom according to an embodiment of the present disclosure comprises a hollow body having two ends and defining an interior space therein; and at least one housing provided at least at one end of the hollow body. A positron-emitting radiation source is provided in each housing. The positron-emitting radiation source is held inside the housing that is comprised of a radiation absorbing material. Each housing is configured to be switched between an ON configuration and an OFF configuration. When in the ON configuration, the positrons traveling in the direction toward the interior of the hollow body exit the housing and enter the interior space and the remaining positron emissions are absorbed by the housing. When in the OFF configuration, all positron emission from the radiation source are absorbed by the housing. When in the ON configuration, the bulk of the positrons entering the hollow body strike the wall of said body, and annihilation gamma photons are created in the wall of the hollow body.

BRIEF DESCRIPTION OF THE DRAWINGS

FIG. 2A is a schematic illustration of an embodiment of the housing for the positron radiation source used in the PET calibration phantom of the present disclosure, where the housing is in its ON configuration.

FIG. 2B is a schematic illustration of the housing of FIG. 2A in its OFF configuration.

DETAILED DESCRIPTION

This description of the exemplary embodiments is intended to be read in connection with the accompanying drawings, which are to be considered part of the entire written description.

Figure 1:
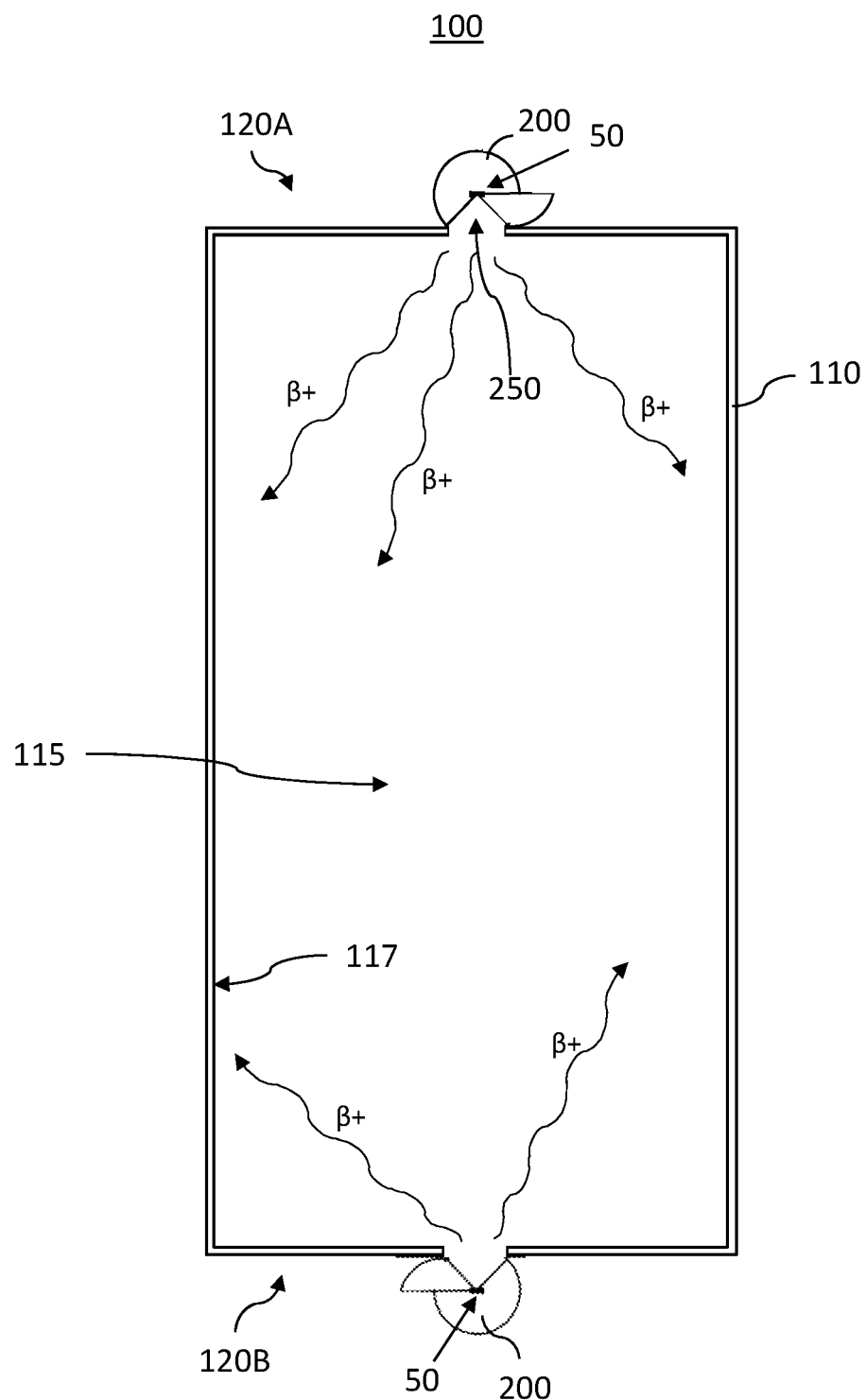
FIG. 1 is a schematic illustration of an embodiment of the PET calibration phantom of the present disclosure.

Referring to FIG. 1, disclosed is a PET calibration phantom 100 comprising a hollow body 110 having two ends 120A and 120B, and defining an interior space 115 therein. The interior space 115 is defined by the inner wall surface 117 of the hollow body 110. A housing 200 (or 300 shown in FIG. 3A) for holding a positron emitting radiation source 50 material is provided at one or both of the two ends 120A and 120B.

Each housing 200 (300) is configured so that when a positron (β+) emitting radiation source 50 is placed inside the housing 200 (300), many of the positrons from the radiation source 50 will leave the housing 200 and enter the interior space 115 by direct emission or scattering but no positrons will be emitted or scattered outside the phantom 100.

The radiation source 50 can be $^{68}$Ge. The radiation source 50 can be provided in any desired shape but preferably, the radiation source 50 is thin enough to allow the positrons emitting in the desired direction, which is the direction toward the interior space 115, to escape the source 50 with minimal self-absorption and minimal absorption within any encapsulating cover. The radiation source 50 can be as thin as physically possible to fabricate. In some embodiments, the radiation source 50 can be in the form of a thin layer. A thin layer of the radiation source 50 can be formed on a suitable substrate by one of a variety of known metal deposition processes, including for example the evaporation of a chelating agent to which radioactive metal atoms, e.g. germanium, are bound. In some embodiments, the radioactive metal atoms can be applied via a bonding agent such as an epoxy or paint.

Each housing 200 (300) comprises an opening 250 directed toward the interior space 115 of the hollow body, thus allowing the positrons from the radiation source 50 to enter the interior space 115. The housing 200 (300) blocks the positrons from emitting or being scattered to outside the housing 200 (300) in other directions or to outside the phantom 100. The housing 200 (300) is comprised of one or more radiation absorbing materials of appropriate thickness to stop the positrons emitted from the radiation source 50. The radiation absorbing materials for the housing 200 (300) enclosing the radiation source 50 are preferably high atomic number materials such as lead, tungsten, tantalum, thorium, gold, stainless steel, bismuth, or uranium, as some examples. In some embodiments, the housing 200 (300) is preferably made of tungsten.

When the PET calibration phantom 100 is not being used, the positron-emitting radiation source 50 can be removed from the housing 200 and stored in an appropriate storage that is properly shielded to contain the annihilation gamma, as well as the positron, radiation. Because just the positron-emitting radiation source 50 needs to be stored in a radiation shielding storage rather than the whole phantom, handling of this PET calibration phantom is easier than the conventional solid fill $^{68}$Ge phantoms. The handling and storage of the remaining structure, the PET calibration phantom shell, is also very simple because there is no radiation to deal with.

Referring to FIGS. 2A, 2B, 3A, and 3B, in some embodiments, the housing 200 (300) can be configured to be switched between an ON configuration and an OFF configuration. In the ON configuration, the opening 250 allows the positrons to leave the housing 200 (300) and travel into and through the interior space 115 of the hollow body to annihilate in the wall of the interior space. In the OFF configuration, the opening 250 is closed off with a radiation absorbing material similar to the housing 200 (300) material and no positrons escape the housing 200 (300).

In some embodiments, the housing 200 (300) can be configured to be switched between the ON configuration and the OFF configuration by a manual operation. In some embodiments, the switching can be controlled remotely. For example, the housing 200 (300) can be configured with an appropriate actuation mechanism that is remotely activated to switch the housing 200 (300) between the ON and the OFF configurations.

FIG. 2A is a schematic side view illustration of an embodiment of the housing 200 in its ON configuration. FIG. 2B is a schematic side view illustration of the housing 200 in its OFF configuration. In this embodiment, the housing 200 comprises at least two portions: a stationary storage portion 210 for holding the radiation source 50; and a movable portion 220. Both portions 210 and 220 are made of a radiation absorbing material as discussed above. The movable portion 220 is configured to be moved or slid back and forth between the ON configuration and the OFF configuration as noted by the arrows S1 and S2. The housing 200 can be switched from the ON configuration to the OFF configuration by moving the movable portion 220 in the direction of the arrow S1. Moving the movable portion 220 in the direction of the arrow S2 does the reverse. The stationary storage portion 210 is configured to hold the radiation source 50 and surrounds it from the side opposite from the interior space 115 of the hollow housing 110 so that all β+ emissions traveling in direction other than toward the interior space 115 are absorbed by the housing 200 and no β+ emissions escape the phantom. The movable portion 220 is provided with an opening 250 that allows the β+ emissions from the radiation source 50 to leave the housing 200 in the direction noted by the arrow A toward the interior space 115. In the OFF configuration shown in FIG. 2B, the movable portion 220 has been shifted over so that the hole 250 is no longer aligned with the radiation source 50. Thus, the radiation source 50 is completely encased inside the housing 200 and no β+ emissions escape from the housing 200.

Figures 3A, 3B:
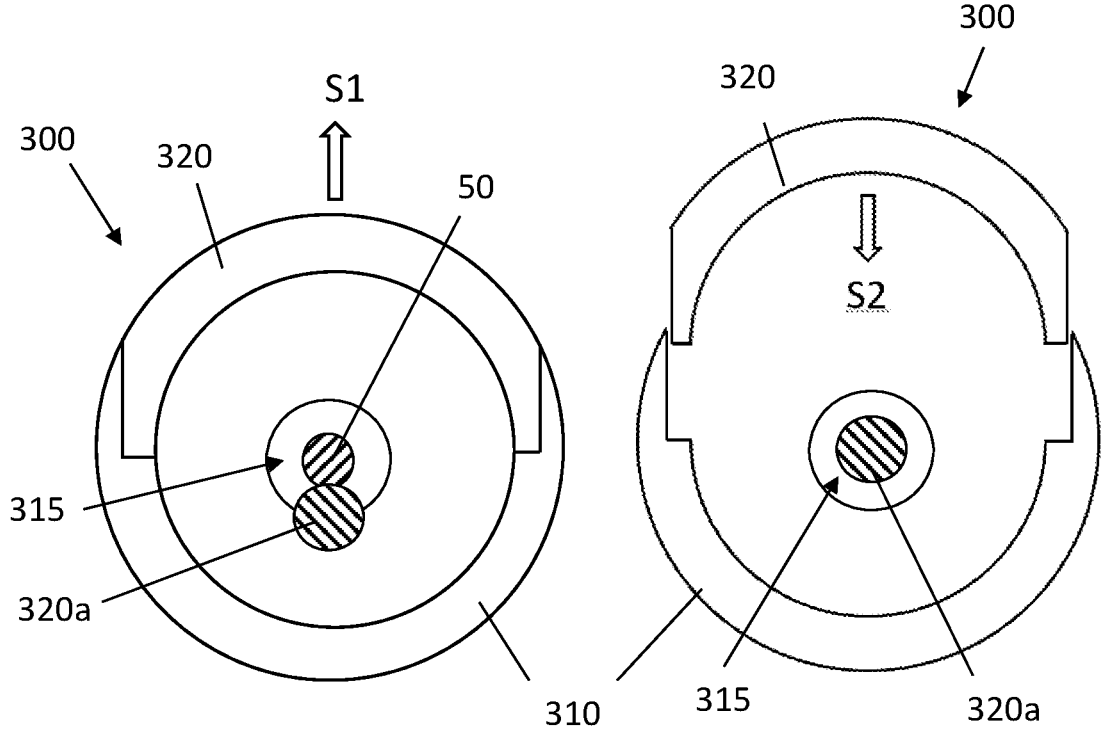
FIG. 3A is a schematic illustration of another embodiment of the housing for the positron radiation source used in the PET calibration phantom of the present disclosure, where the housing is in its ON configuration.
FIG. 3B is a schematic illustration of the housing of FIG. 3A in its OFF configuration.

FIG. 3A is a schematic head-on view illustration of another embodiment of the housing 300 in its ON configuration. FIG. 3B is a schematic head-on view illustration of the housing 300 in its OFF configuration. Head-on view means that the views are looking straight on at the housing 300 from the interior space 115 of the hollow body 110. The housing 300 comprises at least two portions: a stationary storage portion 310 for holding the radiation source 50; and a movable portion 320. Both portions 310 and 320 are made of a radiation absorbing material as discussed above. The movable portion 320 is configured to be moved back and forth between the ON configuration and the OFF configuration as noted by the arrows S1 and S2. The stationary storage portion 310 is configured to hold the radiation source 50 and surrounds it from the side opposite from the interior space 115 of the hollow housing 110 so that all β+ emissions traveling in direction other than toward the interior space 115 is absorbed by the housing 300 and no β+ emissions escape the phantom.

Referring to FIGS. 3A and 3B, the stationary storage portion 310 is provided with a recess 315 within which the radiation source 50 is situated. The movable portion 320 further comprises a cover portion 320a that is configured to cover and seal the radiation source 50 inside the recess 315 when the housing 300 is in its OFF configuration shown in FIG. 3B. In the ON configuration of FIG. 3A, the cover portion 320a is moved aside and exposes the radiation source 50 allowing the β+ radiation to enter the interior space 115 of the phantom 100. The cover portion 320a is connected to the movable portion 320 so that it moves with the movable portion 320 between the ON configuration and the OFF configuration. There can be a variety of structural configurations that can enable the coordinated movement between the movable portion 320 and the cover portion 320a. The structural details of such configuration would be well known to those skilled in the arts.

The hollow body 110 can have any desired shape. However, in preferred embodiments, the hollow body 110 has a cylindrical shape which provides radial symmetry consistent with the imaging volume of most PET systems. The hollow body 110 can be made of any material that is light enough to make it convenient to handle, which maintains well its shape, and whose walls are thick enough to stop all positrons impinging upon it. For example, aluminum, stainless steel, copper, tantalum, or a variety of plastic can be used for the hollow body 110. In preferred examples, polyethylene is used as it is readily available, inexpensive, sufficiently light and durable. Regardless of what material is used, the hollow body 110 should be formed to have walls of sufficient thickness to stop the positrons.

The interior space 115 of the hollow body can be atmospheric air, vacuum or filled with low-density material such as polystyrene foam (e.g. thermal insulating foam) depending on where in the phantom structure one intends the positron annihilation to occur. In embodiments where the interior space 115 is vacuum or filled with air, the emitted positrons from the radiation source 50 can travel essentially unimpeded until they strike the inner wall surface 117 of the hollow body 110. In embodiments where the interior space 115 is filled with air, most of the positrons will travel through the interior space 115 until they reach the inner wall surface 117 and annihilate within the wall 110 and some will annihilate in the air. The positron's annihilation results in 511 keV annihilation gamma photon pairs that can be detected by the PET scanner. Most of the annihilation photon pairs comes from the hollow body wall 110 that stops the positrons. There is very little or no attenuation of the annihilation photon pairs because they are not absorbed nor scattered by the low density fill material. In comparison, in the conventional solid urethane phantom, because of attenuation within the solid urethane, only about 20% of the emitted annihilation photon pairs reach the PET scanner detectors without being absorbed or scattered, with concomitant loss of energy and change of direction. In some embodiments, if the positron annihilation is desired within the interior space 115 of the phantom and not just within the wall 110 of the phantom, the interior space 115 can be filled with a low-density foam material.

The radiation sources 50 emit positrons in all directions and 50% or more of the positrons emitted will be in the desired direction through the opening 250 of the housing 200 toward the interior space 115 of the hollow body 110. The positron emission in other directions are immediately absorbed, or scattered into the hollow body, by the housing 200 material. The phantom 100 of the present disclosure produces a net gain of annihilation photon pairs for the PET scanner to detect compared to the conventional solid urethane phantom. Because positrons have longer range in air or low density foam than in solid urethane, there is essentially very little attenuation of the positrons in the novel phantom 100 of the present disclosure before the positrons strike the inner wall 117 of the hollow body 110, where the annihilation photon pairs are generated.

In some embodiments, one or more positron lenses can be incorporated with the housing 200 to direct more of the positrons emitted by the radiation source 50 in the direction toward the interior of the hollow body 110. Such positron lenses are well known in the art. One example is described in J. Van Klinken, et al., "Mini-Orange Spectrometers for In- and Off-beam Observation of Conversion Electrons," Nuclear Instruments and Methods 130, 427-441 (1975).

A positron emission tomography (PET) calibration phantom shell is also disclosed. Such shell is comprised of a hollow body 110 having two ends 120A, 120B and defining an interior space 115 therein. A housing 200 (or 300) is provided at least at one of the two ends, where the housing is configured to hold a positron-emitting radiation source 50. The housing is comprised of a radiation absorbing material, where the housing is configured to be switched between an ON configuration and an OFF configuration. When the housing is holding a positron-emitting radiation source 50 and the housing is in the ON configuration, the positrons emitted from the radiation source that are traveling in the direction toward the interior of the hollow body exit the housing and enter the interior space and the remaining positron emissions are absorbed by the housing; and when the housing is holding a positron-emitting radiation source 50 and the housing is in the OFF configuration, all positron emission from the radiation source are absorbed by the housing.

The PET calibration phantom of the present disclosure has many benefits over the conventional solid fill $^{68}$Ge phantoms. The disclosed phantom is substantially lighter than the conventional phantom because it is hollow, so it is much easier to handle. Even the embodiment that is filled with foam is substantially lighter than the conventional solid fill cylinder phantom. Because smaller amount of the radiation is necessary and the radiation source can be turned off, the technologists handling the phantom are exposed to substantially reduced dose of radiation. The more efficient use of the radiation reduces the cost associated with the isotope used. Because the radiation source is confined in the radiation absorbing housing 200, 300, the phantom might be stored without additional radiation shielding. Also, because the hollow phantom 100 of the present disclosure has a long positron range, the phantom can be made larger than the conventional, solid PET quality control phantoms, and be able to fill the field of view of the PET scanner with no or minimal scattering of the 511 keV annihilation gamma photon pairs.

In some other embodiments, the concept of the hollow phantom 100 of the present disclosure can be integrated into the PET scanner structure. For example, the tunnel of the PET scanner can be used in lieu of the hollow body 110 of the phantom 100. In such embodiments, the positron radiation source 50 sealed in a housing similar to the housings 200 (300) and positioned at one end or at both ends of the scanner tunnel with the housing's opening 250 aimed into the tunnel. The positrons will annihilate within the tunnel walls producing annihilation photons. Because the exact location and dimensions of the scanner tunnel is already known, the resulting PET image of the tunnel walls serve as a phantom. The scanning and image processing software of the PET scanner would not need to be changed.

Although the subject matter has been described in terms of exemplary embodiments, it is not limited thereto. Rather, the appended claims should be construed broadly, to include other variants and embodiments, which may be made by those skilled in the art.

What is claimed is:

1. A positron emission tomography (PET) calibration phantom comprising:
   a hollow body having two ends and defining an interior space therein;
   a housing provided at least at one of the two ends; and
   a positron-emitting radiation source provided in the housing;
      wherein the housing is comprised of a radiation absorbing material;
      wherein the housing is configured to be switched between an ON configuration and an OFF configuration,
         wherein when in the ON configuration, the positrons emitted from the radiation source that are traveling in the direction toward the interior of the hollow body exit the housing and enter the interior space, and the remaining positron emissions are absorbed by the housing, and when in the OFF configuration, all positron emission from the radiation source are absorbed by the housing,
      whereby the positrons entering the hollow body strike the wall of the hollow body, and 511-keV annihilation gamma photons are created in the wall of the hollow body.

2. The PET calibration phantom of claim 1, wherein a housing is provided at each of the two ends of the hollow body and a positron-emitting radiation source is provided in each of the two housings.

3. The PET calibration phantom of claim 1, wherein the hollow body has a cylindrical shape.

4. The PET calibration phantom of claim 1, wherein the radiation absorbing material enclosing the source is a high atomic number material sufficient to stop positrons emitted from the radiation source.

5. The PET calibration phantom of claim 4, wherein the high atomic number material comprises at least one of gold, tungsten, tantalum, thorium, lead, stainless steel, bismuth, or uranium.

6. The PET calibration phantom of claim 1, wherein the positron-emitting radiation source comprises $^{68}$Ge.

7. The PET calibration phantom of claim 6, wherein the positron-emitting radiation source has a thickness that is sufficiently thin allowing as much of the positrons emitted in a direction toward the interior space of the hollow body to escape the positron-emitting source without being absorbed within the radiation source.

8. The PET calibration phantom of claim 1, wherein the hollow body is made of a material that has a thickness sufficient to stop the positrons.

9. The PET calibration phantom of claim 8, wherein the hollow body is made from aluminum, copper, stainless steel, tantalum, or polyethylene.

10. The PET calibration phantom of claim 8, wherein the hollow body is made from stainless steel.

11. The PET calibration phantom of claim 1, wherein the interior of the hollow body is vacuum, filled with air, or filled with a low-density foam.

12. The PET calibration phantom of claim 1, wherein the housing comprises one or more positron lenses to direct more positrons toward the interior of the hollow body.

13. A positron emission tomography (PET) calibration phantom shell comprising:
   a hollow body having two ends and defining an interior space therein;
   a housing provided at least at one of the two ends, wherein the housing is configured to hold a positron-emitting radiation source;
      wherein the housing is comprised of a radiation absorbing material;
   wherein the housing is configured to be switched between an ON configuration and an OFF configuration, wherein when the housing is holding a positron-emitting radiation source and the housing is in the ON configuration, the positrons emitted from the radiation source that are traveling in the direction toward the interior of the hollow body exit the housing and enter the interior space and the remaining positron emissions are absorbed by the housing; and
   when the housing is holding a positron-emitting radiation source and the housing is in the OFF configuration, all positron emission from the radiation source are absorbed by the housing.

14. The PET calibration phantom shell of claim 1, wherein a housing is provided at each of the two ends of the hollow body.

15. The PET calibration phantom shell of claim 13, wherein the hollow body has a cylindrical shape.

16. The PET calibration phantom shell of claim 13, wherein the radiation absorbing material is a high atomic number material sufficient to stop positrons emitted from the radiation source.

17. The PET calibration phantom shell of claim 16, wherein the high atomic number material comprises at least one of gold, tungsten, tantalum, thorium, lead, stainless steel, bismuth, or uranium.

18. The PET calibration phantom shell of claim 13, wherein the hollow body is made of a material that has a thickness sufficient to stop the positrons.

19. The PET calibration phantom shell of claim 13, wherein the hollow body is made from aluminum, copper, stainless steel, tantalum, or polyethylene.

20. The PET calibration phantom shell of claim 13, wherein the hollow body is made from stainless steel.

21. The PET calibration phantom shell of claim 13, wherein the interior of the hollow body is vacuum, filled with air, or filled with a low-density foam.

22. The PET calibration phantom shell of claim 13, wherein the housing comprises one or more positron lenses that can direct positrons toward the interior of the hollow body when the housing is holding a positron-emitting radiation source.

* * * * *